United States Patent
Helminen et al.

(10) Patent No.: US 11,130,763 B2
(45) Date of Patent: Sep. 28, 2021

(54) METHOD FOR PREPARING A BICYCLIC GUANIDINE AND ITS DERIVATIVES

(71) Applicant: Helsingin yliopisto, Helsingin yliopisto (FI)

(72) Inventors: Jussi Helminen, Helsingin yliopisto (FI); Alistair King, Helsingin yliopisto (FI); Ilkka Kilpeläinen, Helsingin yliopisto (FI)

(73) Assignee: Helsingin Yliopisto, Helsingin Yliopisto (FI)

( * ) Notice: Subject to any disclaimer, the term of this patent is extended or adjusted under 35 U.S.C. 154(b) by 0 days.

(21) Appl. No.: 16/762,522

(22) PCT Filed: Nov. 8, 2018

(86) PCT No.: PCT/FI2018/050823
§ 371 (c)(1),
(2) Date: May 8, 2020

(87) PCT Pub. No.: WO2019/092319
PCT Pub. Date: May 16, 2019

(65) Prior Publication Data
US 2020/0270256 A1 Aug. 27, 2020

(30) Foreign Application Priority Data
Nov. 8, 2017 (FI) .................................... 20175999

(51) Int. Cl.
*C07D 487/04* (2006.01)
*C07C 277/02* (2006.01)
*C07C 277/08* (2006.01)

(52) U.S. Cl.
CPC .................................. *C07D 487/04* (2013.01)

(58) Field of Classification Search
CPC ..................................................... C07D 487/04
See application file for complete search history.

(56) References Cited

FOREIGN PATENT DOCUMENTS

| WO | WO2011079041 A1 | 6/2011 |
|---|---|---|
| WO | WO2011112594 A1 | 9/2011 |
| WO | WO2012116080 A1 | 8/2012 |
| WO | WO2013163130 A1 | 10/2013 |

OTHER PUBLICATIONS

Bell et al: Superbase-derived protic ionic liquids with chelating fluorinated anions. Tetrahedron Lett., May 20, 2011, vol. 52, No. 29, pp. 3723-3725.

Nowicki et al: Novel basic ionic liquids from cyclic guanidines and amidines—new catalysts for transesterification of oleochemicals. Journal Chem. Technol. Biotechnol., Jun. 12, 2013, vol. 89, pp. 48-55.

Usachev et al: Convenient preparation of bicyclic guanidines. Synthetic Comm., Jul. 30, 2011. vol. 41, No. 24, pp. 3683-3688.

*Primary Examiner* — Susanna Moore
(74) *Attorney, Agent, or Firm* — Laine IP Oy

(57) ABSTRACT

The present invention relates to a method of producing a bicyclic guanidine and its derivatives. In particular, the present invention relates to a method of producing triazabicyclodecene (TBD) and its derivatives, particularly alkyl derivatives, such as methyl triazabicyclodecene (MTBD), and MTBD-derived ionic liquids. The invention also relates to the use of said compounds in cellulose dissolution and subsequent processing.

19 Claims, 1 Drawing Sheet

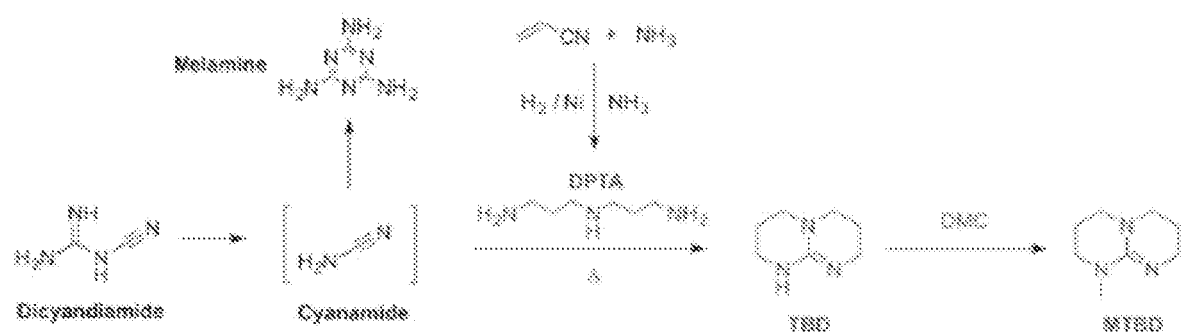

METHOD FOR PREPARING A BICYCLIC GUANIDINE AND ITS DERIVATIVES

FIELD

The present invention relates to a method of producing a bicyclic guanidine and its derivatives. In particular, the present invention relates to a method of producing triazabicyclodecene (TBD) and its derivatives, particularly alkyl derivatives, such as methyl triazabicyclodecene (MTBD), and MTBD-derived ionic liquids. The invention also relates to the use of said compounds in cellulose dissolution and processing.

BACKGROUND

Triazabicyclodecene or 1,5,7-triazabicyclo[4.4.0]dec-5-ene (TBD) is a bicyclic strong guanidine base. It is an organic superbase, which is used as an organocatalyst and metal ligand precursor with potential wide applications as such for a variety of base-mediated organic transformations. For example, it is a known catalyst for esterification, epoxy resin formation and cyclic carbonate ring-opening chemistry.

The methyl derivative of TBD (MTBD) and MTBD-derived ionic liquids (acid-base conjugates) find use particularly in cellulose dissolving applications. MTBD-derived ionic liquids, [mTBDH][OAc] in particular, have been determined to be much more hydrolytically stable than ionic liquids previously used for cellulose dissolution, for example [DBNH][OAc].

The synthesis of TBD, its methyl derivative (MTBD) and associated ionic liquids has been thoroughly studied.

WO 2011/112594 A1 describes synthesis of TBD from dicyandiamide and bis(3-aminopropyl)amine (or dipropylene triamine, DPTA) in the presence of a weak acid, using a near stoichiometric amount of carbon dioxide as the acid. The disclosed synthesis is carried out in the presence of added solvents and yields TBD in salt form. WO 2011/079041 A1 discloses a method for the preparation polycyclic guanidines wherein a triamine compound is reacted with guanidine, cyanamide or melamine compounds in a solvent. The method yields TBD as a salt, such as mesylate or carbonate. In the method of WO 2012/116080 A1, bicyclic guanidine salts are prepared in aqueous media by reacting a guanidine carbonate salt or dicyandiamide with an acid and dipropylene triamine.

Finally, WO 2013/163130 A1 discloses a method for producing 1,5,7-triazabicyclo[4.4.0]dec-5-ene by reaction of a disubstituted carbodiimide, dipropylene triamine, and an ethereal solvent and/or an alcohol.

In the current method TBD is obtained as a free base, unlike in previous methods where TBD is typically obtained in its salt form. This allows for easy workup and methylation (derivatization) as there is no need to release TBD from the salt form prior to methylation. Also, it is thus possible to obtain various salts of TBD allowing it to react with an acid. Moreover, the existing methods for synthesis of TBD involve considerable costs associated with synthesis and purification steps while the yields are only mediocre or low. Further, many of the prior art methods also involve toxic reagents or produce by-products that are difficult to separate or may themselves be hazardous.

There is thus an overall need of a cost effective preparation process of TBD for the further conversion to MTBD and to MTBD-derived ionic liquids, without the formation of undesired by-products. MTBD-derived ionic liquids are designed for example for the purpose of cellulose dissolution and subsequent processing, e.g. Lyocell-type fibre spinning or chemical modification.

SUMMARY OF THE INVENTION

It is an object of the invention to provide a novel synthesis method of bicyclic guanidines, particularly TBD, to maximise yields and reduce costs related with synthesis and costly purification steps.

It is also an object of the invention to provide a novel synthesis method of TBD, which avoids formation of significant amounts of undesired by-products and yields TBD in base form, ready for isolation or further processing. The TBD obtained in base form by the method of the invention and its methylated derivative MTBD have also a high purity.

A still further object of the invention is to provide a novel synthesis method of bicyclic guanidines, particularly TBD, which is essentially free of added solvents.

According to a first aspect of the present invention, there is provided a method for preparing bicyclic guanidines, particularly 1,5,7-triazabicyclo[4.4.0]dec-5-ene (TBD), and its derivatives, which method comprises the steps of contacting a cyanamide and a polyamine, in particular in a liquid phase formed by the polyamine, at an elevated temperature to cause said cyanamide to react with said polyamine.

According to a second aspect of the present invention, there is provided the use of the bicyclic guanidines or their derivatives produced by a method according to the present invention for producing analogs or conjugates thereof, particularly ionic liquids or acid-base conjugates.

According to a third aspect of the present invention, there are provided ionic liquids comprising the compounds formed in accordance with the method of the invention, particularly for use in cellulose dissolution.

The invention is defined by the features of the independent claims. Some specific embodiments are defined in the dependent claims.

Considerable advantages are achieved by the present invention. Thus the present synthesis method maximises yields and reduces costs associated with current synthesis and purification steps of bicyclic guanidines, particularly TBD.

Further, the method avoids formation of significant amounts of melamine as an unwanted side product while yielding TBD in base form, ready for isolation or further processing. There is thus no need of liberating TBD from stoichiometric or near stoichiometric amounts of salt-forming acids. (e.g. HCl, p-toluenesulfonic acid, carbonate, hydrogen carbonate or carbonic/carbamic acid derivatives).

The invention also provides increased stability of MTBD-derived ionic liquids with fibre-spinning. Increased stability means that the recycling of the ionic liquids is much more effective.

BRIEF DESCRIPTION OF THE DRAWINGS

FIG. 1 illustrates a reaction scheme to MTBD in accordance with at least some embodiments of the present invention. FIG. 1 also shows that DPTA can be prepared at low cost from ammonia and acrylonitrile.

EMBODIMENTS

Definitions

In the present context, the term "bicyclic guanidine" refers to a guanidine consisting of unsubstituted or substituted rings comprising at least 5 members, i.e. atoms located in the ring structure. The bicyclic guanidine may thus have for example a 5-member ring, a 6-member ring and/or a 7-member ring. The number of members in each ring of the cyclic guanidine can be either the same or different.

In the present context, the "derivatives" of the bicyclic guanidine include but are not limited to compounds wherein one or more of the ring atoms of the bicyclic guanidine are substituted with a substituent group, such as alkyl, substituted alkyl, alkenyl, hydroxyalkyl, alkoxy or substituted alkoxy, mono- or dialkyl amino, aminoalkyl or substituted aminoalkyl group. Derivatives of the bicyclic guanidine also include substituted or unsubstituted bicyclic guanidines, which have been further processed to form e.g. acid-base conjugates (ionic liquids).

The present technology, including the embodiments discussed in more detail below, is suitable for preparing bicyclic guanidines and their derivatives, particularly TBD and its derivatives, such as alkyl derivatives.

In the present context, the term "alkyl" refers to saturated, straight or branched hydrocarbon radicals containing one to eight carbon atoms. In certain embodiments, alkyl groups contain 1-6 carbon atoms, or 1-5 carbon atoms. In some embodiments, alkyl groups contain 1-4 carbon atoms, 1-3 carbon atoms, or 1-2 carbon atoms. Examples of alkyl radicals include, but are not limited to, methyl, ethyl, n-propyl, isopropyl, n-butyl, isobutyl, pentyl, hexyl, and the like.

The term "alkenyl", as used herein, refers to straight or branched hydrocarbon radicals having at least one carbon-carbon double bond. In certain embodiments, alkenyl groups contain 2-12 carbon atoms. In some embodiments, alkenyl groups contain 2-8 carbon atoms, 2-6 carbon atoms, or 2-5 carbon atoms. In some embodiments, alkenyl groups contain 2-4 carbon atoms, or 2-3 carbon atoms. Examples of alkenyl radicals include, but are not limited to, ethenyl, propenyl, butenyl, 1-methyl-2-buten-1-yl, and the like.

In an embodiment of the invention, a cyanamide and a polyamine are contacted at an elevated temperature to react said cyanamide with said polyamine to form a bicyclic guanidine.

A cyanamide refers to cyanamide and dicyandiamide or 2-cyanoguanidine, preferably to dicyandiamide.

A polyamine is preferably a triamine but it may also be a tetramine. Examples of suitable polyamines include but are not limited to bis(3-aminopropyl)amine or dipropylene triamine (DPTA), diethylene triamine, triethylene tetramine, tripropylene tetramine, ethylene propylene triamine, 3-(2-aminoethylamino)propylamine, or combinations thereof.

An "elevated temperature" refers to a temperature range that includes the boiling point of the polyamine at the applied pressure, for example at atmospheric pressure or at overpressure. In an embodiment of the invention, the temperature range is 150-250° C., for example 180-230° C., in particular 220-230° C. To avoid formation of undesired by-products, such as melamine, it is preferred to perform the reaction at a temperature above about 150° C.

The time a reaction is allowed to proceed can be adjusted to maximize the yield of the desired product and to minimize the formation of by-products. Such adjustments are readily apparent to a person skilled in the art. By way of an example, the reaction time of dicyandiamide with DPTA may vary from 0.5 hours to 24 hours, or preferably from 4 to 8 hours.

In one embodiment, the invention makes use of the novel finding that bis(3-aminopropyl)amine or dipropylene triamine (DPTA) is an unexpectedly good solvent for dicyandiamide (DCD), which is hard to solubilise otherwise.

Surprisingly, DPTA dissolves DCD in an amount over the stoichiometric ratio of the reaction. In one embodiment, another unexpectedly good solvent for dicyandiamide is 3-(2-aminoethylamino)propyl amine (N3-amine), which dissolves DCD in an amount over the stoichiometric ratio of the reaction. Other complex solvents would require additional purification steps, which would significantly add to the overall cost.

In one embodiment, the method of the present invention thus comprises contacting dicyandiamide (DCD) with bis(3-aminopropyl)amine (DPTA) in particular in liquid phase. Preferably, DCD is contacted in a liquid phase which consists of or consists essentially of bis(3-aminopropyl) amine. As discussed above, the reaction takes place at an elevated temperature, and preferably in the presence of an amount of polyamine, which is over the stoichiometric ratio of the reaction.

In preferred embodiments, cyanamide is thus contacted with a stoichiometric excess of polyamine, in particular with a molar amount of the polyamine, which is 1.5 to 1000 times, for example 2 to 500 times, in particular 2 to 50 times, for example 3 to 10 times the molar amount of cyanamide.

In another embodiment, the method of the invention comprises contacting dicyandiamide (DCD) with 3-(2-aminoethylamino)propylamine (N3-amine), in particular in liquid phase, which consists of or consists essentially of N3-amine.

When contacting dicyandiamide with DPTA or N3-amine, dicyandiamide may be added stepwise in powder form or, alternatively, in liquid form as a DPTA or N3-amine solution. As a typical by-product of the reaction, gaseous ammonia is formed. In some embodiments, the ammonia can be recovered and recycled, thereby eliminating a possible waste stream.

In one embodiment, the method of the invention comprises dissolving a cyanamide in a first solution of the polyamine, and stepwise adding said solution to a second solution of the polyamine, wherein the second solution of the polyamine is kept at an elevated temperature.

In one embodiment, contacting a cyanamide with a polyamine takes place in the presence of an acid catalyst. Suitable acid catalysts may include but are not limited to mineral acids such as hydrochloric, sulphuric, or phosphoric acid, and organic acids, for example sulfonic acids or acetic acids. Suitable sulfonic acids include alkyl or aryl sulfonic acids, which are known to a person skilled in the art. Exemplary sulfonic acids include but are not limited to methane sulfonic acid, trifluoromethane sulfonic acid and p-toluene sulfonic acid and mixtures thereof. Suitable acetic acids include, but are not limited to, fluoroacetic acids, such as trifluoroacetic acid. However, the method of the invention can be accomplished without adding an acid catalyst or in the presence of small amounts of the acid catalyst.

In an embodiment of the invention, synthesis of TBD is carried out by contacting dicyandiamide (DCD), preferably in bis(3-aminopropyl)amine (DPTA) solution, with DPTA and preferably an acid catalyst (e.g. p-toluenesulfonic acid) at a high temperature (e.g. 220° C.) to yield TBD and gaseous ammonia as side product.

The method of the invention comprises also an embodiment wherein dicyandiamide is dissolved in a first solution of bis(3-aminopropyl)amine, and the first solution comprising bis(3-aminopropyl)amine and dicyandiamide is stepwise added to a second solution of bis(3-aminopropyl)amine, which is kept at a temperature of at least 150° C., preferably at least 200° C.

In an embodiment, dicyandiamide is dissolved in a liquid phase formed by bis(3-aminopropyl)amine to form a solution, and the dicyandiamide and the bis(3-aminopropyl) amine are reacted in the presence of an acid catalyst to yield TBD. The acid catalyst can be added before or after the addition of the dicyanamide into the liquid phase formed by bis(3-aminopropyl)amine.

Preferably, the acid catalyst used is soluble in bis(3-aminopropyl)amine, in which case, a homogeneous reaction mixture is obtained.

Typically, in the above embodiments, no or a small amount of melamine is formed as a side product of the reaction. The term "no melamine" is to be interpreted such that the amount of melamine is less than 2 wt-%, preferably less than 0.2 wt-%, of the liquid phase after completion of reaction.

In one embodiment, the reaction scheme to MTBD is as illustrated in FIG. 1.

Alkylation of TBD to its alkyl derivatives, such as methyl and ethyl derivatives, can be carried out by mixing TBD with an appropriate solvent and adding alkylating reagent(s), such as alkyl carbonates, alkyl halides, alkyl sulfates, alkyl sulfonates, or alkyl phosphonates. Methylation of TBD to MTBD is thus carried out for example by reacting TBD with a methyl carbonate, methyl halide, methyl sulfate, methyl sulfonate, or methyl phosphonate. Analogous ethylating reagents are suitable for ethylation of TBD.

In one embodiment, methylation of TBD is carried out with dimethyl carbonate.

It is possible to carry out the method of the invention batchwise or as a continuous process.

The TBD or its methyl derivative MTBD formed in accordance with the method of the invention can be obtained in extremely pure form. In some embodiments, the TBD obtained by the method of the invention may be subjected to sublimation, distillation or crystallization.

With the method of the invention yields of TBD above 60%, or above 65-70%, are obtainable. Moreover, the method produces considerably smaller amounts of undesired by-products, particularly melamine, than prior art processes for the preparation of TBD.

Surprisingly, in the method of the invention, DPTA may act as both a reagent and a solvent, and thus no external solvent needs to be added to the reaction mixture. Alternatively, for example in a continuous process, the ammonia formed in the reaction may act as a solvent of the cyanamide.

The preparation of TBD in a cost effective manner and subsequent conversion to MTBD and then to MTBD-derived ionic liquids (acid-base conjugates) provides advantages in cellulose dissolution. Said ionic liquids are designed for the purpose of cellulose dissolution and subsequent processing, e.g. lyocell-type fibre-spinning or chemical modification. MTBD-derived ionic liquids, [mTBDH][OAc] in particular, have been determined to be much more hydrolytically stable than previous IONCELL-F generations, e.g. [DBNH][OAc].

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Experimental

Example 1

A two liter three-necked flask fitted with dropping funnel, a thermostat temperature probe and an Allihn condenser topped by a bubbler, was charged with a stirring magnet and 594 grams (4.53 mol) of DPTA containing 4.31 grams (0.0227 mol) of toluenesulphonic acid monohydrate. The flask was flushed with argon, the mixture stirred vigorously and heated to an internal temperature of 220° C. using the thermostat. A solution of 140 grams (1.67 mol) of dicyandiamide in 280 g (2.13 mol) of DPTA containing 2.03 grams (0.0107 mol) of toluenesulphonic acid monohydrate was added dropwise through the dropping funnel over six hours. Towards the end of addition the temperature was increased to 230° C. to maintain the rate of evolution of ammonia. After the addition excess DPTA was recovered from the mixture by distillation under reduced pressure to give a pale residue containing 356 grams of TBD (2.55 mol, yield 76.7% of theoretical).

Example 2

A crude product prepared as in example 1 was dissolved in 350 ml of hot toluene. The mixture was heated to 100° C. in a distillation apparatus fitted with a Vigreux column, and dimethyl carbonate was added to the mixture until boiling point of 100° C. was reached. Methanol and $CO_2$ were removed from the mixture by distillation along with some dimethyl carbonate and toluene, while more dimethyl carbonate was dropped in to maintain the boiling point. When NMR analysis showed complete conversion, excess dimethyl carbonate was stripped from the mixture under reduced pressure. The mixture was diluted with 2 liters of toluene and cooled down, the toluene phase decanted and toluene removed by rotary evaporation. The residue was distilled under vacuum to give MTBD (302 g, yield 77.1% of theoretical).

Example 3

A three-necked flask was charged with a stirring magnet and 732.8 grams (4.78 mol) of MTBD. An addition funnel was fitted on the flask, the apparatus purged with argon and 287.2 grams (4.78 mol) of glacial acetic acid added from the addition funnel in a rapid pace to reach and maintain a temperature of 85-100° C., to give 1020 grams of yellowish [mTBDH][OAc] solidifying at 80-83° C.

Example 4

9.05 grams of [mTBDH][OAc] and stirring magnet were introduced into a 20 ml vial, heated at 85° C. with stirring. 1.02 grams of Avicel PH-101 (microcrystalline cellulose) was added to the vial to result in a clear yellow solution of cellulose.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

TBD is an organic superbase with wide applications as such. It is also a known catalyst for several chemical reactions. Synthesis of TBD and its derivatives, particularly MTBD and associated ionic liquids, finds use in chemical companies ranging from fine chemicals producers to bulk synthesis, MTBD-derived ionic liquids are used in cellulose dissolution and fibre spinning where they provide increased stability and thus cost effective recycling of the ionic liquids.

ACRONYMS LIST

DCD dicyandiamide
DPTA bis(3-aminopropyl)amine or dipropylene triamine
IL ionic liquid
MTBD 7-methyl-1,5,7-triaza[4.4.0]bicyclodec-5-ene
TBD 1,5,7-triaza[4.4.0]bicyclodec-5-ene

CITATION LIST

Patent Literature

WO 2011/112594 A1
WO 2011/079041 A1
WO 2012/116080 A1
WO 2013/163130 A1

The invention claimed is:

1. A method for preparing an unsubstituted or substituted bicyclic guanidine in base form comprising contacting a cyanamide and a polyamine at an elevated temperature to cause said cyanamide to react with said polyamine, wherein the method is essentially free of added solvents and yields the unsubstituted or substituted bicyclic guanidine in base form, and wherein the method occurs in one reaction step.

2. The method according to claim 1, wherein the unsubstituted or substituted bicyclic guanidine consists of unsubstituted or substituted rings comprising at least 5 members or ring atoms, wherein the number of members in each ring is either the same or different.

3. The method according to claim 1, wherein the substituted bicyclic guanidine comprises a compound wherein one or more of the ring atoms of the bicyclic guanidine is substituted with a substituent group selected from alkyl, substituted alkyl, alkenyl, hydroxyalkyl, alkoxy or substituted alkoxy, mono- or dialkylamino, aminoalkyl or substituted aminoalkyl group.

4. The method according to claim 1, wherein the method prepares an unsubstituted or substituted 1,5,7-triazabicyclo[4.4.0]dec-5-ene (TBD).

5. The method according to claim 1, wherein the cyanamide comprises a dicyandiamide.

6. The method according to claim 1, wherein the polyamine comprises a triamine or a tetramine, selected from bis(3-aminopropyl)amine or dipropylene triamine (DPTA), diethylene triamine, triethylene tetramine, tripropylene tetramine, ethylene propylene triamine, 3-(2-aminoethylamino)propylamine, or combinations thereof.

7. The method according to claim 6, wherein the polyamine comprises a triamine, and wherein the triamine comprises bis(3-aminopropyl)amine or dipropylene triamine (DPTA).

8. The method according to claim 6, wherein the polyamine comprises 3-(2-aminoethylamino)propylamine.

9. The method according to claim 1, wherein the cyanamide is dissolved in a first solution of the polyamine and said first solution is stepwise added to a second solution of the polyamine, wherein the second solution of the polyamine is kept at the elevated temperature.

10. The method according to claim 1, wherein the elevated temperature is the boiling point of the polyamine at an applied pressure.

11. The method according to claim 1, wherein the elevated temperature is 150-250° C.

12. The method according to claim 1, wherein the cyanamide is contacted with the polyamine in the presence of an acid catalyst.

13. A method for preparing an unsubstituted or substituted 1,5,7-triazabicyclo[4.4.0]dec-5-ene TBD) comprising the step of contacting dicyandiamide with bis(3-aminopropyl)amine in a bis(3-aminopropyl)amine solution at a temperature of at least 150° C. to cause said dicyandiamide to react with said bis(3-aminopropyl)amine wherein the method is essentially free of added solvents and yields the unsubstituted or substituted TBD in base form, and wherein the method occurs in one reaction step.

14. The method according to claim 13, wherein a first solution of bis(3-aminopropyl)amine comprises the dicyandiamide, and the first solution comprising bis(3-aminopropyl)amine and dicyandiamide is stepwise added to a second solution of bis(3-aminopropyl)amine, which is kept at a temperature of at least 150° C.

15. The method according to claim 13, wherein the temperature is 150-250° C.

16. The method according to claim 13, which is essentially free of added solvents.

17. The method according to claim 13, wherein the step of contacting dicyandiamide with bis(3-aminopropyl)amine is performed in the presence of an acid catalyst.

18. The method according to claim 1, wherein less than 2 wt-% melamine is formed as a side product of the reaction.

19. The method according to claim 1, wherein the method prepares an alkyl derivative of 1,5,7-triazabicyclo[4.4.0]dec-5-ene (TBD).

\* \* \* \* \*